United States Patent
Slayton et al.

(10) Patent No.: US 7,530,958 B2
(45) Date of Patent: May 12, 2009

(54) METHOD AND SYSTEM FOR COMBINED ULTRASOUND TREATMENT

(75) Inventors: Michael H. Slayton, Tempe, AZ (US); Inder Raj S. Makin, Loveland, OH (US); Peter G. Barthe, Phoenix, AZ (US)

(73) Assignee: Guided Therapy Systems, Inc., Mesa, AZ (US)

( * ) Notice: Subject to any disclaimer, the term of this patent is extended or adjusted under 35 U.S.C. 154(b) by 674 days.

(21) Appl. No.: 10/950,112

(22) Filed: Sep. 24, 2004

(65) Prior Publication Data

US 2006/0074355 A1 Apr. 6, 2006

(51) Int. Cl.
*A61H 1/00* (2006.01)
(52) U.S. Cl. .......................................................... 601/2
(58) Field of Classification Search ................. 601/2–4; 600/437, 439
See application file for complete search history.

(56) References Cited

U.S. PATENT DOCUMENTS

| | | | |
|---|---|---|---|
| 4,343,301 A * | 8/1982 | Indech | 601/3 |
| 4,381,007 A | 4/1983 | Doss | |
| 4,858,613 A | 8/1989 | Fry | |
| 4,875,487 A | 10/1989 | Seppi | |
| 4,917,096 A | 4/1990 | Englehart et al. | |
| 4,951,653 A | 8/1990 | Fry | |
| 4,955,365 A | 9/1990 | Fry | |
| 4,976,709 A | 12/1990 | Sand | |
| 5,036,855 A | 8/1991 | Fry | |
| 5,054,470 A | 10/1991 | Fry | |
| 5,115,814 A | 5/1992 | Griffith et al. | |
| 5,117,832 A | 6/1992 | Sanghvi | |
| 5,150,711 A | 9/1992 | Dory | |
| 5,163,421 A | 11/1992 | Bernstein | |
| 5,191,880 A * | 3/1993 | McLeod et al. | 601/2 |
| 5,230,334 A | 7/1993 | Klopotek | |
| 5,269,297 A | 12/1993 | Weng et al. | |
| 5,282,797 A | 2/1994 | Chess | |
| 5,304,169 A | 4/1994 | Sand | |
| 5,370,121 A | 12/1994 | Reichenberger et al. | |
| 5,458,596 A | 10/1995 | Lax et al. | |
| 5,492,126 A | 2/1996 | Hennige | |

(Continued)

FOREIGN PATENT DOCUMENTS

JP 3123559 5/1991

(Continued)

OTHER PUBLICATIONS

International Search Report dated Dec. 23, 2006 issued in corresponding PCT case, Application No. PcT/US2005/034358.

*Primary Examiner*—Eric F Winakur
*Assistant Examiner*—Helene Bor
(74) *Attorney, Agent, or Firm*—Snell & Wilmer LLP

(57) ABSTRACT

A non-invasive method and system for combined ultrasound treatment are provided. An exemplary combined ultrasound treatment system comprises a transducer configured to deliver ultrasound energy to provide two or more energy effects to a region of interest. The energy effects facilitate the initiation of one or more responses in the region of interest. In accordance with an exemplary embodiment of the present invention, a transducer is configured to deliver energy over varying temporal and/or spatial distributions in order to provide energy effects and initiate responses in a region of interest.

28 Claims, 11 Drawing Sheets

U.S. PATENT DOCUMENTS

| | | | |
|---|---|---|---|
| 5,524,620 A | 6/1996 | Rosenschein et al. | |
| 5,526,815 A | 6/1996 | Granz et al. | |
| 5,558,092 A * | 9/1996 | Unger et al. | 600/439 |
| 5,601,526 A * | 2/1997 | Chapelon et al. | 601/3 |
| 5,676,692 A | 10/1997 | Sanghvi | |
| 5,755,753 A | 5/1998 | Knowlton | |
| 5,762,066 A | 6/1998 | Law | |
| 5,871,524 A | 2/1999 | Knowlton | |
| 5,873,902 A | 2/1999 | Sanghvi | |
| 5,904,659 A | 5/1999 | Duarte | |
| 5,938,612 A | 8/1999 | Kline-Schoder | |
| 5,968,034 A | 10/1999 | Fullmer | |
| 5,971,949 A | 10/1999 | Levin | |
| 5,984,882 A | 11/1999 | Rosenschein | |
| 6,071,239 A | 6/2000 | Cribbs | |
| 6,093,883 A | 7/2000 | Sanghvi | |
| 6,113,558 A | 9/2000 | Rosenschein | |
| 6,113,559 A | 9/2000 | Klopotek | |
| 6,135,971 A | 10/2000 | Hutchinson | |
| 6,183,773 B1 | 2/2001 | Anderson | |
| 6,190,323 B1 | 2/2001 | Dias et al. | |
| 6,190,336 B1 | 2/2001 | Duarte | |
| 6,241,753 B1 | 6/2001 | Knowlton | |
| 6,273,864 B1 | 8/2001 | Duarte | |
| 6,315,741 B1 | 11/2001 | Martin et al. | |
| 6,325,769 B1 * | 12/2001 | Klopotek | 601/2 |
| 6,361,531 B1 | 3/2002 | Hissong | |
| 6,377,855 B1 | 4/2002 | Knowlton | |
| 6,381,498 B1 | 4/2002 | Knowlton | |
| 6,409,720 B1 | 6/2002 | Hissong | |
| 6,413,253 B1 | 7/2002 | Koop | |
| 6,413,254 B1 | 7/2002 | Hissong | |
| 6,428,477 B1 * | 8/2002 | Mason | 600/437 |
| 6,428,532 B1 * | 8/2002 | Doukas et al. | 606/9 |
| 6,436,061 B1 | 8/2002 | Costantino | |
| 6,438,424 B1 | 8/2002 | Knowlton | |
| 6,443,914 B1 | 9/2002 | Costantino | |
| 6,500,121 B1 | 12/2002 | Slayton et al. | |
| 6,500,141 B1 | 12/2002 | Irion | |
| 6,511,428 B1 | 1/2003 | Azuma et al. | |
| 6,514,244 B2 | 2/2003 | Pope | |
| 6,595,934 B1 | 7/2003 | Hissong | |
| 6,607,498 B2 | 8/2003 | Eshel | |
| 6,623,430 B1 | 9/2003 | Slayton et al. | |
| 6,626,854 B2 | 9/2003 | Friedman | |
| 6,626,855 B1 | 9/2003 | Weng et al. | |
| 6,645,162 B2 | 11/2003 | Friedman | |
| 6,685,640 B1 | 2/2004 | Fry | |
| 6,692,450 B1 | 2/2004 | Coleman | |
| 6,719,694 B2 | 4/2004 | Weng | |
| 6,749,624 B2 | 6/2004 | Knowlton | |
| 6,932,771 B2 | 8/2005 | Whitmore et al. | |
| 6,936,046 B2 | 8/2005 | Hissong | |
| 6,976,492 B2 | 12/2005 | Ingle et al. | |
| 6,997,923 B2 | 2/2006 | Anderson | |
| 7,020,528 B2 | 3/2006 | Neev | |
| 7,063,666 B2 | 6/2006 | Weng | |
| 7,094,252 B2 | 8/2006 | Koop | |
| 7,179,238 B2 | 2/2007 | Hissong | |
| 7,258,674 B2 | 8/2007 | Cribbs et al. | |
| 7,273,459 B2 | 9/2007 | Desilets | |
| 7,347,855 B2 | 3/2008 | Eshel et al. | |
| 2001/0009997 A1 | 7/2001 | Pope | |
| 2002/0040199 A1 | 4/2002 | Klopotek | |
| 2002/0055702 A1 | 5/2002 | Atala et al. | |
| 2002/0082528 A1 | 6/2002 | Friedman | |
| 2002/0082589 A1 | 6/2002 | Friedman | |
| 2002/0169442 A1 | 11/2002 | Neev | |
| 2003/0032900 A1 | 2/2003 | Ella | |
| 2003/0040739 A1 | 2/2003 | Koop | |
| 2003/0050678 A1 | 3/2003 | Sierra et al. | |
| 2003/0065313 A1 | 4/2003 | Koop | |
| 2003/0083536 A1 | 5/2003 | Eshel | |
| 2003/0176790 A1 | 9/2003 | Slayton et al. | |
| 2003/0191396 A1 | 10/2003 | Sanghvi | |
| 2003/0212351 A1 | 11/2003 | Hissong | |
| 2003/0216795 A1 | 11/2003 | Harth et al. | |
| 2003/0220536 A1 | 11/2003 | Hissong | |
| 2004/0015106 A1 | 1/2004 | Coleman | |
| 2004/0030227 A1 | 2/2004 | Littrup et al. | |
| 2004/0039312 A1 | 2/2004 | Hillstead | |
| 2004/0039418 A1 | 2/2004 | Elstrom et al. | |
| 2004/0059266 A1 | 3/2004 | Fry | |
| 2004/0206365 A1 | 10/2004 | Knowlton | |
| 2004/0210214 A1 | 10/2004 | Knowlton | |
| 2004/0217675 A1 | 11/2004 | Desilets | |
| 2005/0055073 A1 | 3/2005 | Weber | |
| 2005/0154314 A1 | 7/2005 | Quistgaard | |
| 2005/0154332 A1 | 7/2005 | Zanelli et al. | |
| 2005/0187495 A1 | 8/2005 | Quistgaard | |
| 2005/0261584 A1 | 11/2005 | Eshel | |
| 2005/0267454 A1 | 12/2005 | Hissong | |
| 2006/0074313 A1 | 4/2006 | Slayton et al. | |
| 2006/0074314 A1 | 4/2006 | Slayton et al. | |
| 2006/0079868 A1 | 4/2006 | Makin et al. | |
| 2006/0089632 A1 | 4/2006 | Barthe et al. | |
| 2006/0089688 A1 | 4/2006 | Panescu | |
| 2006/0111744 A1 | 5/2006 | Makin et al. | |
| 2006/0116671 A1 | 6/2006 | Slayton et al. | |
| 2006/0122508 A1 | 6/2006 | Slayton et al. | |
| 2006/0122509 A1 | 6/2006 | Desilets | |
| 2006/0184069 A1 * | 8/2006 | Vaitekunas | 601/2 |
| 2006/0241440 A1 | 10/2006 | Eshel | |
| 2006/0241442 A1 | 10/2006 | Barthe et al. | |
| 2007/0032784 A1 | 2/2007 | Gliklich et al. | |
| 2007/0035201 A1 | 2/2007 | Desilets | |
| 2007/0055156 A1 | 3/2007 | Desilets | |

FOREIGN PATENT DOCUMENTS

| | | |
|---|---|---|
| JP | 4089058 | 3/1992 |
| JP | 7080087 | 3/1995 |
| JP | 7222782 | 8/1995 |
| WO | WO9735518 | 10/1997 |
| WO | WO9933520 | 7/1999 |
| WO | WO9949788 | 7/1999 |
| WO | WO0015300 | 3/2000 |
| WO | WO0021612 | 4/2000 |
| WO | WO0128623 | 4/2001 |
| WO | WO0182777 | 8/2001 |
| WO | WO0182778 | 11/2001 |
| WO | WO0187161 | 11/2001 |
| WO | WO0209813 | 2/2002 |
| WO | WO0224050 | 3/2002 |
| WO | WO02092168 | 11/2002 |
| WO | WO03070105 | 8/2003 |
| WO | WO03077833 | 9/2003 |
| WO | WO03099177 | 12/2003 |

* cited by examiner

METHOD AND SYSTEM FOR COMBINED ULTRASOUND TREATMENT

FIELD OF INVENTION

This invention generally relates to a therapeutic ultrasound method and system, and more particularly, to a method and system for combined ultrasound treatment.

BACKGROUND OF THE INVENTION

Many conventional applications of energy to superficial human tissue employ ablative or non-ablative lasers, radio frequency, or ultrasound. Some recent examples of such applications include that disclosed in Knowlton, U.S. Pat. No. 6,381,498 (using radio-frequency (RF), microwave or ultrasound for wrinkle reduction), in Friedman, U.S. Pat. No. 6,626,854 (employing ultrasound for lipolysis), and in Klopotek, U.S. Pat. Nos. 6,113,559 and 6,325,769 (employing ultrasound for collagen reformation). While surface ablative lasers cause severe trauma to the upper layer of the skin, such as dermis and stratum corneum, and realize a long recovery time and eventual rejuvenation of the skin, the medical efficacy and results are significant. Non-ablative lasers and RF energy sources do not cause significant trauma to the upper surface of the skin, but the efficacy of such sources is low, and with the end results being less than satisfactory.

During the last decade attempts have been made to use ultrasound in lipolysis procedures for volumetric ablation of the deep fat layer. While laboratory results of such investigative attempts may show potential promise of fat destruction in volume, the objective of such ultrasound procedures is solely to reduce the thickness of the fat layer rather than any rejuvenation of the initial superficial layer.

Currently, some suggested therapy methods aim at collagen reformation as a primary target for reducing wrinkles in the skin, including the use of connective tissue regeneration as a primary target and biological response. However, specific targeting of collagen reformation may not be the only or even a critical factor in tissue rejuvenation. For example diode lasers and intense pulsed light (IPL), which can target collagen with very high specificity, are generally yielding mixed or low efficacy results. Moreover, RF energy deposition is generally volumetric with a high gradient toward the applicator probe and has difficulties with the selectivity and placement of the energy that fundamentally is dependent on the electrical impedance of the treated tissue.

SUMMARY OF THE INVENTION

In accordance with various aspects of the present invention, a non-invasive method and system for combined ultrasound treatment are provided. An exemplary combined ultrasound treatment method and system comprises a transducer configured to deliver ultrasound energy to provide two or more energy effects to a region of interest. The energy effects facilitate the initiation of one or more responses in the region of interest.

In accordance with an exemplary embodiment of the present invention, a transducer is configured to deliver energy over varying temporal and/or spatial distributions in order to provide energy effects and initiate responses in a region of interest. For example, an exemplary transducer is operated under one or more frequency ranges to provide two or more energy effects and initiate one or more responses in the region of interest. In addition, the transducer can also be configured to deliver planar, defocused and/or focused energy to a region of interest to provide two or more energy effects and to initiate one or more biological responses.

BRIEF DESCRIPTION OF THE DRAWING FIGURES

The subject matter of the invention is particularly pointed out and distinctly claimed in the concluding portion of the specification. The invention, however, both as to organization and method of operation, may best be understood by reference to the following description taken in conjunction with the claims and the accompanying drawing figures, in which like parts may be referred to by like numerals:

DETAILED DESCRIPTION

The present invention may be described herein in terms of various components and processing steps. It should be appreciated that such components and steps may be realized by any number of hardware components configured to perform the specified functions. For example, the present invention may be configured with various medical treatment devices, visual imaging and display devices, input terminals and the like, which may carry out a variety of functions under the control of one or more control systems or other control devices. In addition, the present invention may be practiced in any number of medical or treatment contexts and that the exemplary embodiments relating to a method and system for combined ultrasound treatment as described herein are merely a few of the exemplary applications for the invention. For example, the principles, features and methods discussed may be applied to any medical or other tissue or treatment application.

In accordance with various aspects of the present invention, a non-invasive method and system for combined ultrasound treatment are provided. An exemplary therapeutic method and system comprise a transducer system configured to deliver one or more energy fields to one or more regions of interest within a patient. The energy field or fields may provide two or more effects to initiate one or more responses to the region or regions of interest.

Figure 1:
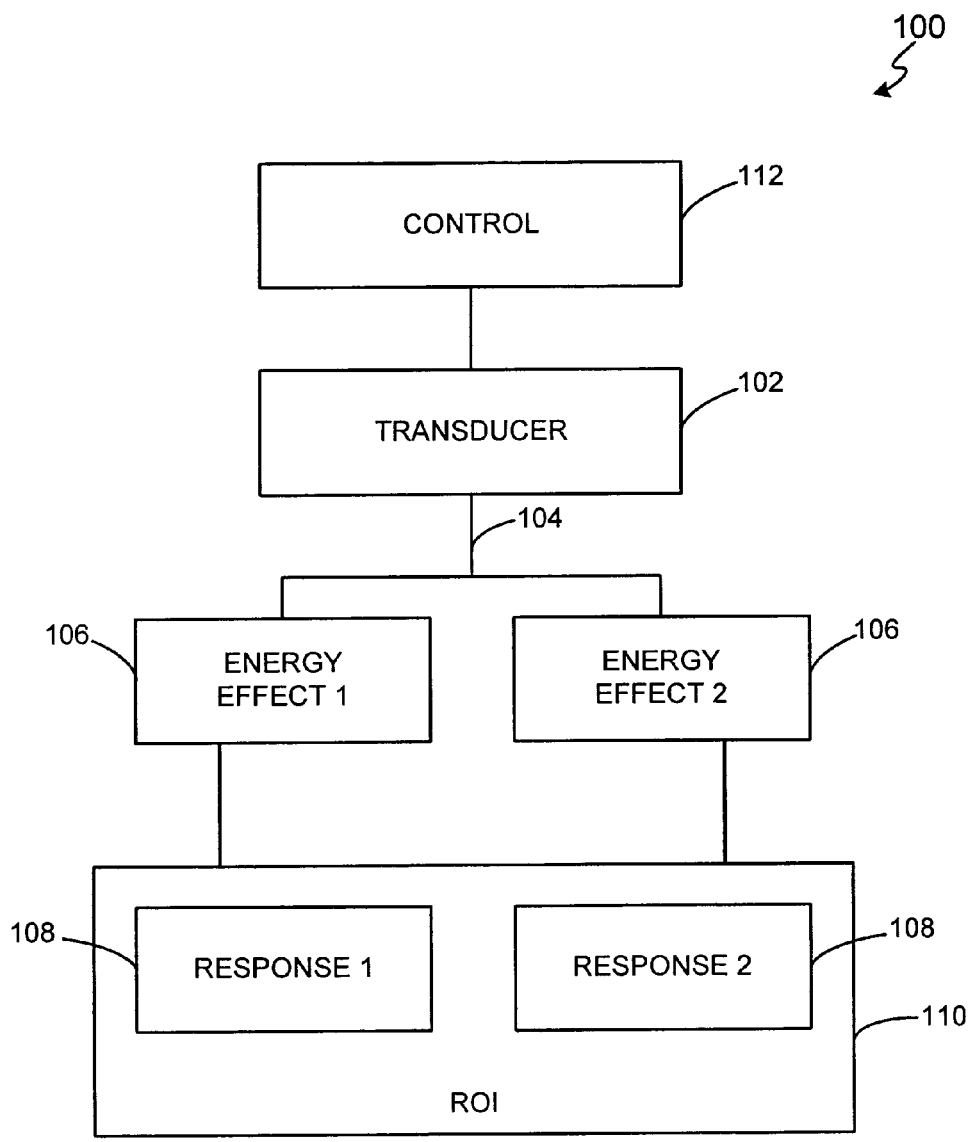
FIG. 1 illustrates a block diagram of an exemplary combined ultrasound treatment system in accordance with an exemplary embodiment of the present invention.

For example, with reference to an exemplary embodiment illustrated in FIG. 1, an exemplary system 100 for combined ultrasound treatment includes a transducer 102 that can be configured via control system 112 to provide one or more energy fields 104 to achieve two or more biological effects 106 for rejuvenation and/or treatment of a region of interest (ROI) 110. Effects 104 can initiate and/or stimulate two or more biological responses 108 within ROI 110.

For example, a combined ultrasound treatment system may be achieved by providing ultrasound treatment under various temporal and/or spatial regimes to initiate and combine a plurality of biological effects to provide one or more responses to a region or regions of interest. By providing ultrasound treatment under various temporal and/or spatial regimes, energy fields 104 can comprise ultrasound energy of any acoustic frequency level. For example, energy fields 104 can comprise a low frequency acoustical energy, an increased intensity homogeneous or uniform ultrasound field of energy, a high-frequency acoustical energy, ultra-high frequency acoustical energy, and/or any other level of acoustical energy. Selecting the frequency for operation can be based on the type of treatment desired for an application. Energy fields 104 can also be focused, defocused, and/or made substantially planar by transducer 102 to provide a plurality of effects 106. For example, a substantially planar energy field 104 can provide a heating and/or pretreatment effect, a focused energy field 104 can provide an ablative or hyperthermal effect, and a defocused energy field can provide diffused heating effects.

Effects 106 can comprise any tissue effect configured for initiating and/or stimulating two or more biological responses 108 in ROI 110, including but not limited to, thermal and non-thermal streaming, cavitational (including stable cavitation by low level ultrasound of 0.1 to 1 W/cm$^2$ in the megahertz frequency range), hydrodynamic, ablative, hemostatic, diathermic, and/or resonance-induced tissue effects. A combination of two or more effects to produce one or more responses can produce a higher efficacy and faster rejuvenation of the skin without causing chronic injury to the human tissue. For example, a combination of variable temporal and/or spatial depositions of ultrasound energy can be provided to tissue underneath the stratum corneum without chronic injury to epidermis and stratum corneum.

Response(s) 108 initiated and/or stimulated by effects 106 can include any biological response initiated and/or stimulated by energy effects, such as, for example: 1) hemostasis, including that stimulated from highly concentrated ultrasound beams, 2) subsequent revascularization/angiogenesis, such as that generated from high frequency applications of approximately 2 MHz to 7 MHz or more, 3) growth of interconnective tissue, 4) reformation and/or ablation of existing tissue such as fat, collagen and others, 5) increased cell permeability that may facilitate the possibility of stimulated gene or medication therapy to tissue, and/or increased permeability of certain tissues to a variety of medications initiated by ultrasound frequencies 10 kHz to 10 MHz, 6) enhanced delivery and/or activation of medicants, 7) stimulation of protein synthesis and/or 8) any other possible tissue response such as coagulative necrorosis. Exemplary ablative responses of focused ultrasound are demonstrated in U.S. Pat. Nos. 6,050,943 and 6,500,121, having at least one common inventor and a common Assignee as the present application. Thus, for example, a low intensity dispersed ultrasound field can be generated to provide for angiogenesis, an increased intensity homogeneous or uniform ultrasound field can be generated to provide for diathermy that increases the rate of healing and rejuvenation, and/or high intensity focused and/or unfocused beams can be generated to provide for temporary ablative and hemostatic effects in a variety of depth and positions of human tissue, whereby a summation or a combined effect of rejuvenation is created by combining ultrasound energy fields.

In providing treatment, transducer 102 may provide therapy, imaging and/or temperature or other tissue parameter monitoring to a region of interest 110. Region of interest 110 can comprise an inner treatment region, a superficial region, a subcutaneous region of interest and/or any other region of interest in between an inner treatment region, a superficial region, and/or a subcutaneous region within a patient. While only one region of interest 110 is depicted, transducer 102 may be configured to treat a plurality of regions of interest.

For example, an exemplary combined transducer system can comprise a transducer configured to provide highly concentrated ultrasound energy to provide effects that initiate and/or stimulate a hemostasis response. An exemplary combined transducer system can also comprise a transducer configured to provide medium frequency range ultrasound energy, ranging from approximately 2 MHz to 7 MHz, to provide effects that initiate and/or stimulate responses such as additional revascularization/angiogenesis treatment, among others. The exemplary therapeutic transducer system can also comprise a transducer configured to deliver energy that provides a non-thermal streaming effect to initiate and/or stimulate a tissue regeneration response. In addition, a transducer may also be configured to initiate and/or stimulate a stable cavitation response through by effects provided from the delivery of low-level ultrasound energy.

Transducer 102 can comprise one or more transducers configured for facilitating treatment. Transducer 102 can also comprise one or more transduction elements. The transduction elements can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In addition to, or instead of, a piezoelectrically active material, transducer 102 can comprise any other materials configured for generating radiation and/or acoustical energy such as capacitively coupled transducers or other acoustic sources. Transducer 102 can also comprise one or more matching and/or backing layers configured along with the transduction element such as coupled to the piezoelectrically active material. Transducer 102 can also be configured with single or multiple damping elements along the transduction element.

In accordance with an exemplary embodiment, the thickness of the transduction element of transducer 102 can be configured to be uniform. That is, the transduction element can be configured to have a thickness that is substantially the same throughout.

In accordance with another exemplary embodiment, the transduction element can also be configured with a variable thickness, and/or as a multiple damped device. For example, the transduction element of transducer 102 can be configured to have a first thickness selected to provide a center operating frequency of a lower range, for example from approximately 1 kHz to 3 MHz. The transduction element can also be configured with a second thickness selected to provide a center operating frequency of a higher range, for example from approximately 3 to 100 MHz or more.

Transducer 102 can be configured as a single broadband transducer excited with at least two or more frequencies to provide an adequate output for generating a desired response 108. Transducer 102 can also be configured as two or more individual transducers, wherein each transducer comprises a transduction element. The thickness of the transduction elements can be configured to provide center-operating frequencies in a desired treatment range. For example, transducer 102 can comprise a first transducer configured with a first transduction element having a thickness corresponding to a center frequency range of approximately 1 MHz to 3 MHz, and a second transducer configured with a second transduction element having a thickness corresponding to a center frequency of approximately 3 MHz to 100 MHz or more. Various other ranges of thickness for a first and/or second transduction element can also be realized.

An exemplary transducer 102 can be suitably controlled and operated in various manners. For example, with reference to an exemplary embodiment depicted in FIG. 2, an exemplary combined ultrasound treatment system 200 may comprise a control system 208 coupled to a transducer 202. Control system 208 may be configured to facilitate control and operation of transducer 202 for providing combined ultrasound treatment to a region of interest 210. To facilitate controlled movement, in accordance with an exemplary embodiment, control system 208 may also be configured with a motion control and position encoding system 212 configured to facilitate mechanical scanning by transducer 202 for providing more flexible ultrasound treatment of a region of interest 210. Motion control and position encoding system 212 can comprise any conventional motion control system, with various types of feedback arrangements in addition to or instead of position encoding. For example, motion control and position encoding system 212 can also comprise one or more feedback configurations or sources of information as disclosed in U.S. patent application Ser. No. 10/944,500 "System and Method for Variable Depth Ultrasound Treatment", filed on Sep. 16, 2004, having at least one common inventor and a common Assignee as the present application, and incorporated herein by reference. The position-encoding configuration can comprise any position encoder system now known or hereinafter devised.

Control system 208 may comprise a processor, a display, and/or one or more input devices. The processor may comprise a personal computer, a Unix system, or any other conventional processing unit. An exemplary display may comprise a monitor, LCD screen, or any other device configured to display an image. The exemplary display may be configured to provide imaging in any manner now known or hereinafter devised. For example, transducer 202 may use pulse-echo imaging to obtain an image of a ROI 210. That image may then be transmitted to the display via one or more coupling mechanisms.

An input/output device may comprise a keyboard, a mouse, a touch-screen, or any other device for the input and/or output of information. The information from the input device and images displayed may be received or transmitted in any format, such as manually, by analog device, by digital device, and/or by any other mechanisms. The various devices of control system 208, including any processor, display, and/or input device, can be coupled together in any manner. By coupling, the various devices may be directly connected to each other or may be connected through one or more other devices or components that allow a signal to travel to/from one component to another. The various coupling components for the devices comprising control system 208 can include but are not limited to the internet, a wireless network, a conventional wire cable, an optical cable or connection through air, water, or any other medium that conducts signals, and any other coupling device or medium.

Figure 2:
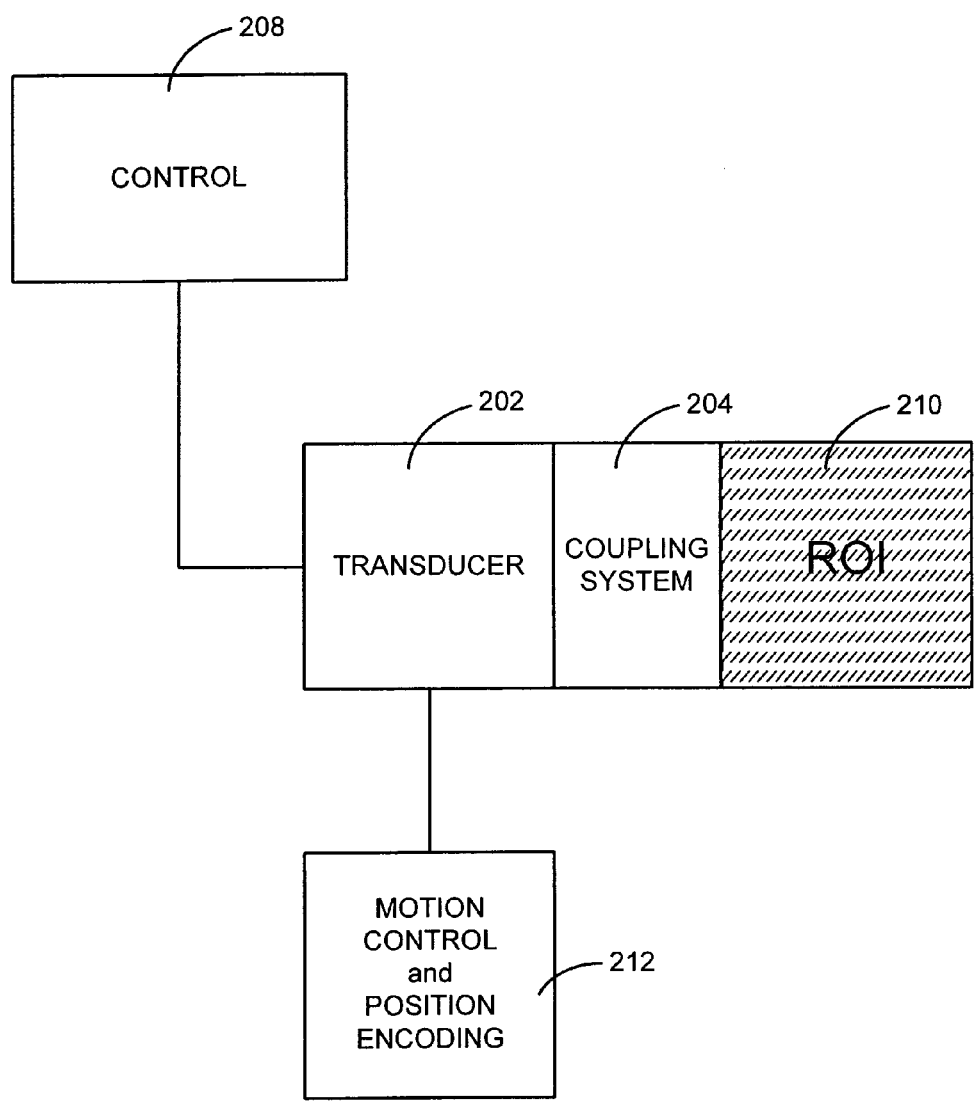
FIG. 2 illustrates a block diagram of an exemplary combined ultrasound treatment system in accordance with an exemplary embodiment of the present invention.

Control system 208 can also be coupled to transducer 202 in various manners. In accordance with an exemplary embodiment, electrical leads may couple together control system 208 and transducer 202. The electrical leads may be configured to enable power to be transmitted to and signals received from transducer 202, and can comprise any wiring type, configuration and/or arrangement for use with ultrasound transducers. Transducer 202 may also be coupled to electrical leads in various manners. For example, while FIG. 2 depicts electrical leads coupled to only one end of transducer 202, electrical leads may also be coupled together on an opposite end, or any other location along transducer 202. Control system 208 may also be configured integral to transducer 202, for example connected together as a single structure with suitable electrical and/or transmission connections in between.

To facilitate coupling of transucer 202 to region of interest 210, transducer 202 can further comprise a coupling system 204 configured for acoustic coupling of ultrasound energy and signals. Coupling system 204 may facilitate such coupling through use of various coupling mediums, including air and other gases, water and other fluids, gels, solids, and/or any combination thereof, or any other medium that allows for signals to be transmitted between transducer 202 and region of interest 210. In addition to providing a coupling function, in accordance with an exemplary embodiment, coupling system 204 can also be configured for providing temperature control during the treatment application. For example, coupling system 204 can be configured for controlled cooling of an interface surface or region between transducer 202 and region of interest 210 by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial and/or thermal energy control of combined ultrasound treatment system 200.

As discussed above, an exemplary transducer 202 can be configured in various manners for providing combined ultrasound treatment to a region-of-interest 210. For example, with reference to an exemplary embodiment depicted in FIG. 3, transducer 302 can be configured as an acoustic array to facilitate phase focusing. That is, transducer 302 can be configured as an array of electronic apertures that may be operated by a variety of phases via variable electronic time delays. By the term "operated," the electronic apertures of transducer 302 may be manipulated, driven, used, and/or configured to produce and/or deliver an energy beam corresponding to the phase variation caused by the electronic time delay. For example, these phase variations can be used to deliver defocused beams, planar beams, and/or focused beams, each of which may be used in combination to achieve different physiological effects in region of interest (ROI) 310. Transducer 302 may additionally be configured with any software and/or other hardware for generating, producing and or driving a phased aperture array with one or more electronic time delays.

Transducer 302 can be configured to produce and/or deliver lower and/or higher frequencies to treat ROI 310. ROI 310 can also comprise one or more additional regions of interest. For example, ROI 310 can comprise a superficial layer 312, a subcutaneous layer 314, and/or an inner region 322 of a patient. ROI 310 can also comprise any area between superficial layer 312 and inner region 322 or between subcutaneous layer 314 and inner region 322. Inner region 322 is located at a depth 324 within tissue layers of a patient. For example, depth 324 can range from approximately 0 mm to 40 mm within a patient, wherein the approximately 0 mm range comprises the outer surface of superficial layer 312 of the patient. In other words, superficial layer 312 of the patient can comprise any area on or near the surface of the patient. Treatment by transducer 302 may include treatment of any of superficial, subcutaneous and/or inner region of a patient, as well as any combination of those regions of a patient. In accordance with one exemplary embodiment, treatment of first ROI 310 may be facilitated by use of transducer 302 driven at low frequencies, for example, from approximately 1 MHz to 3 MHz.

Figure 3:
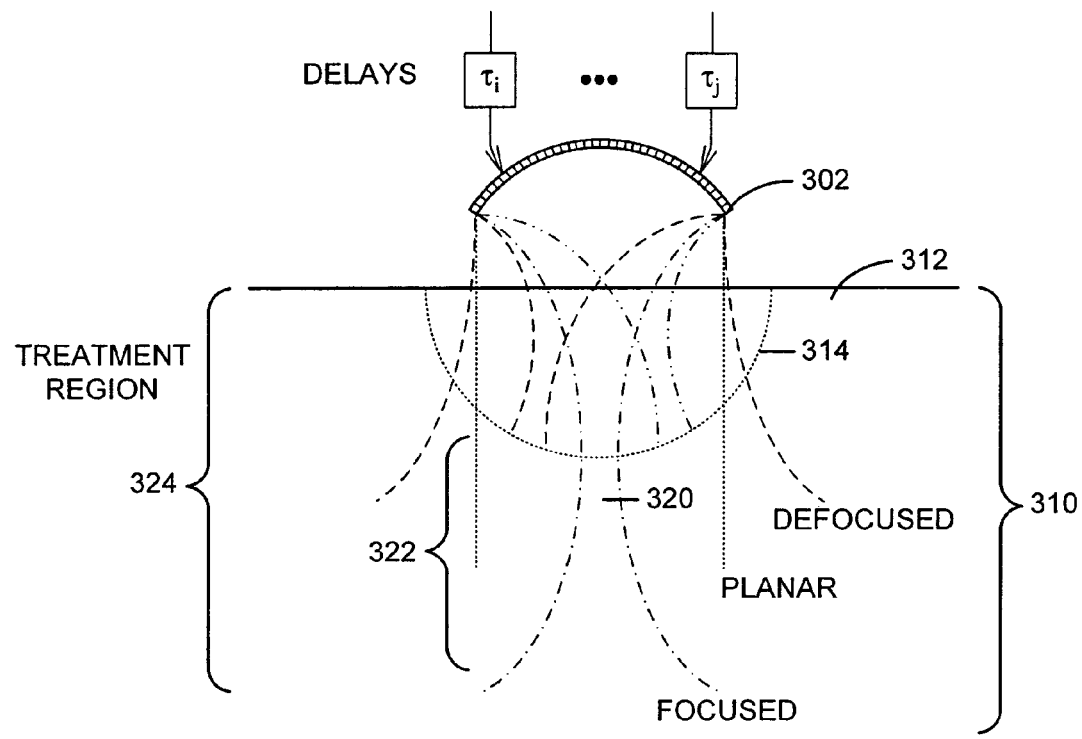
FIG. 3 illustrates a cross-sectional diagram of an exemplary transducer in accordance with an exemplary embodiment of the present invention.

With reference again to an exemplary embodiment depicted in FIG. 3, transducer 302 may also be configured to treat one or more additional regions of interest (ROI) 320. In accordance with an exemplary embodiment, additional ROI 320 may be located within ROI 310. Treatment of additional ROI 320 may be facilitated by use of transducer 302 operating from low to ultra-high frequencies, for example, from below approximately 3 MHz up to 100 MHz or more. While FIG. 3 depicts additional ROI 320 located within inner region 322, in accordance with other exemplary embodiments, additional ROI 320 may be located anywhere within first ROI 310, including within inner region 322, superficial region 312 and/or subcutaneous region 314.

By treatment of ROI 310, with momentary reference again to FIG. 1, transducer 302 may be configured to deliver one or more energy fields 104 to provide a plurality of effects 106 to initiate and/or stimulate one or more biological responses 108, such as, for example, diathermy, hemostasis, revascularization, coagulative necrosis, coagulative necrosis angiogenesis, growth of interconnective tissue, tissue reformation, ablation of existing tissue, protein synthesis and/or enhanced cell permeability. Two or more of these biological responses may be combined to facilitate rejuvenation and/or treatment of superficial tissue. Transducer 302 may also be configured for imaging and/or temperature or other tissue parameter monitoring of ROI 310 in order to facilitate optimal treatment results.

Transducer 302 can also be configured to provide focused treatment to one or more regions of interest using moderate frequencies, ranging from approximately 750 kHz to 10 MHz. In order to provide focused treatment, transducer 302 can be configured with one or more variable depth devices to facilitate treatment. For example, transducer 302 may be configured with variable depth devices disclosed in U.S. patent application Ser. No. 10,944,500, entitled "System and Method for Variable Depth Ultrasound Treatment", and again incorporated herein by reference In addition, transducer 302 can also be configured to treat one or more additional ROI 320 through the enabling of sub-harmonics or pulse-echo imaging, as disclosed in U.S. patent application Ser. No. 10/944, 449, entitled "Method and System for Ultrasound Treatment with a Multi-directional Transducer", filed on Sep. 16, 2004, having at least one common inventor and a common Assignee as the present application, and also incorporated herein by reference.

Moreover, any variety of mechanical lenses or variable focus lenses, e.g. liquid-filled lenses, may also be used to focus and or defocus the sound field. For example, with reference to exemplary embodiments depicted in FIGS. 4A and 4B, transducer 402 may also be configured with an electronic focusing array 404 in combination with one or more transduction elements 406 to facilitate increased flexibility in treating ROI 410. Array 404 may be configured in a manner similar to transducer 302. That is, array 404 can be configured as an array of electronic apertures that may be operated by a variety of phases via variable electronic time delays, for example, $\tau_1, \tau_2, \tau_3 \ldots \tau_j$. By the term "operated," the electronic apertures of array 404 may be manipulated, driven, used, and/or configured to produce and/or deliver energy in a manner corresponding to the phase variation caused by the electronic time delay. For example, these phase variations can be used to deliver defocused beams, planar beams, and/or focused beams, each of which may be used in combination to achieve different physiological effects in ROI 410.

Transduction elements 406 may be configured to be concave, convex, and/or planar. For example, in an exemplary embodiment depicted in FIG. 4A, transduction elements 406A are configured to be concave in order to provide focused energy for treatment of ROI 410. Additional embodiments are disclosed in U.S. patent application Ser. No. 10/944,500, entitled "System and Method for Variable Depth Ultrasound Treatment", and again incorporated herein by reference.

Figure 4A:
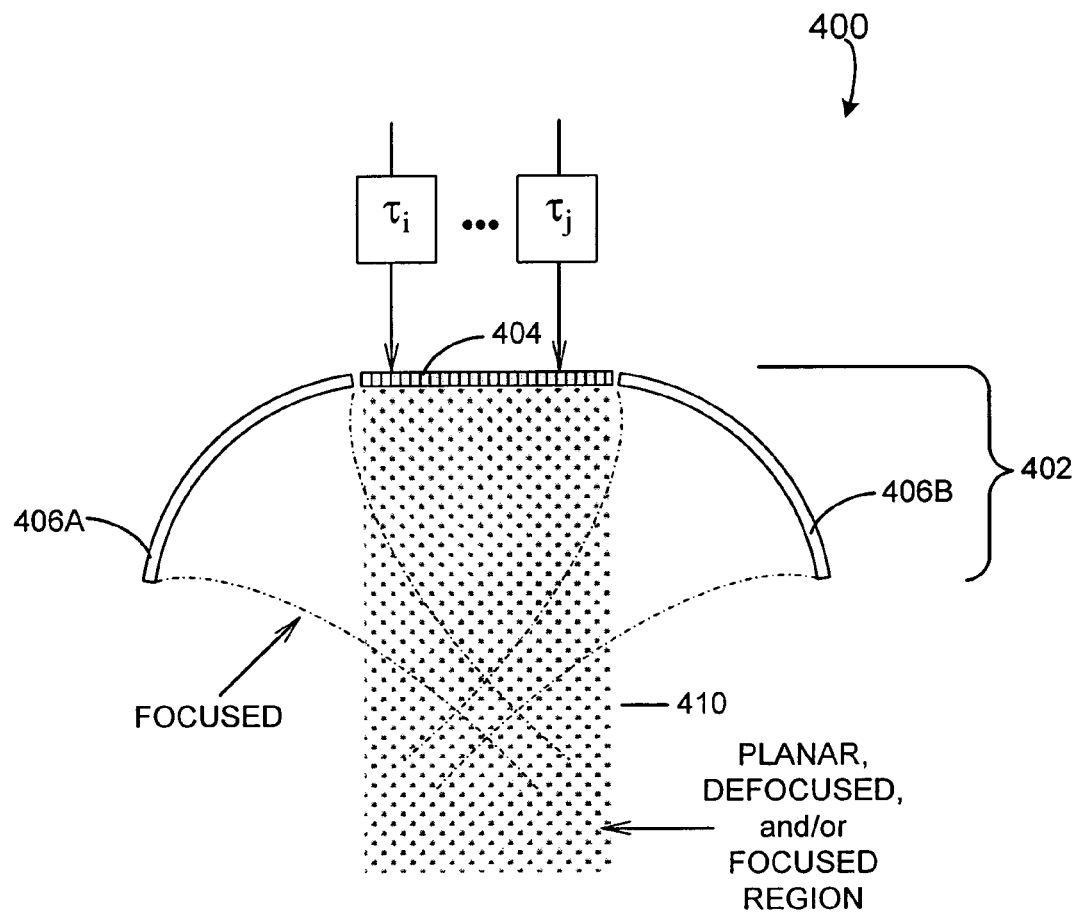
FIGS. 4A, 4B, 4C and 4D illustrate cross-sectional diagrams of an exemplary transducer for imaging in accordance with various exemplary embodiments of the present invention.
Figure 4B:
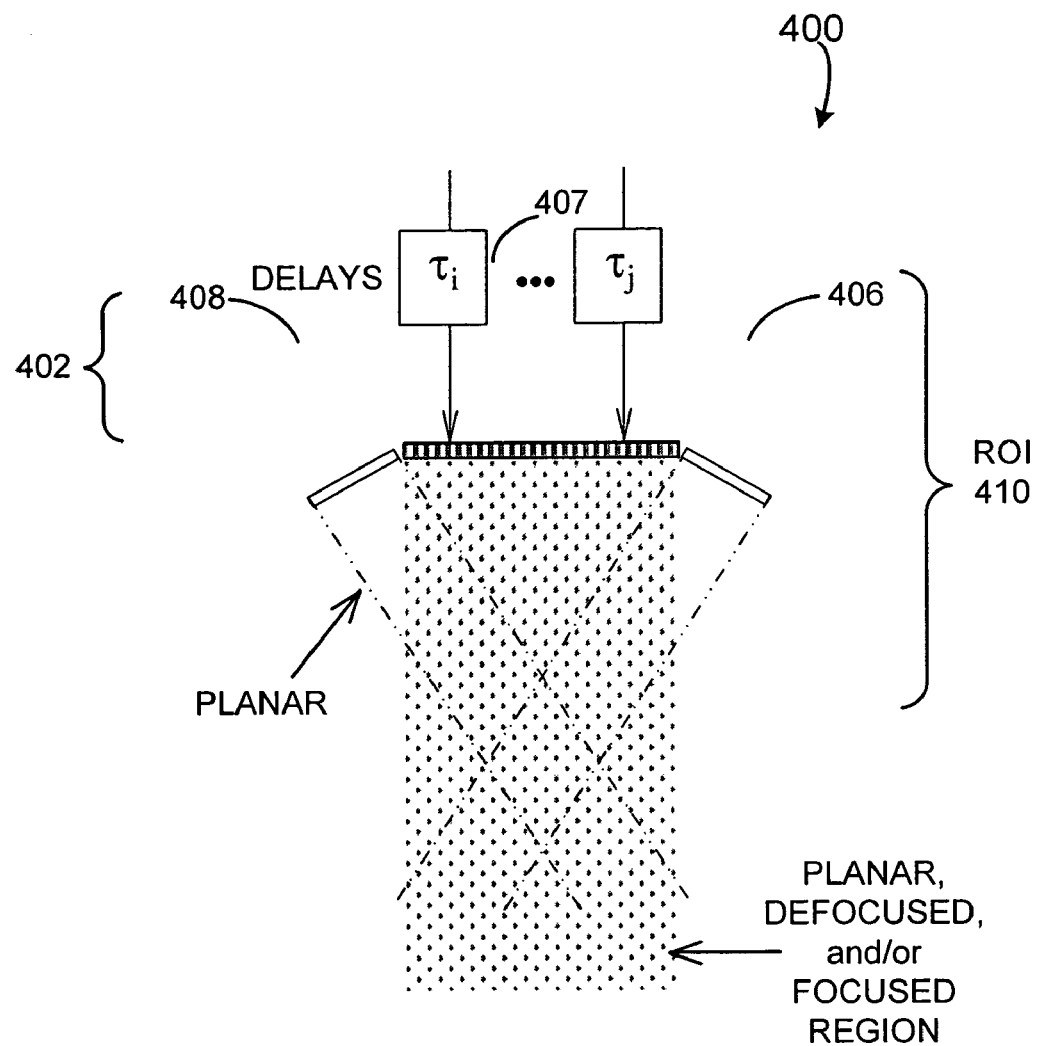

In another exemplary embodiment, depicted in FIG. 4B, transduction elements 406B can be configured to be substantially flat in order to provide substantially uniform energy to ROI 410. While FIGS. 4A and 4B depict exemplary embodiments with transduction elements 404 configured as concave and substantially flat, respectively, transduction elements 404 can be configured to be concave, convex, and/or substantially flat. In addition, transduction elements 404 can be configured to be any combination of concave, convex, and/or substantially flat structures. For example, a first transduction element can be configured to be concave, while a second transduction element can be configured to be substantially flat.

Figure 4C:
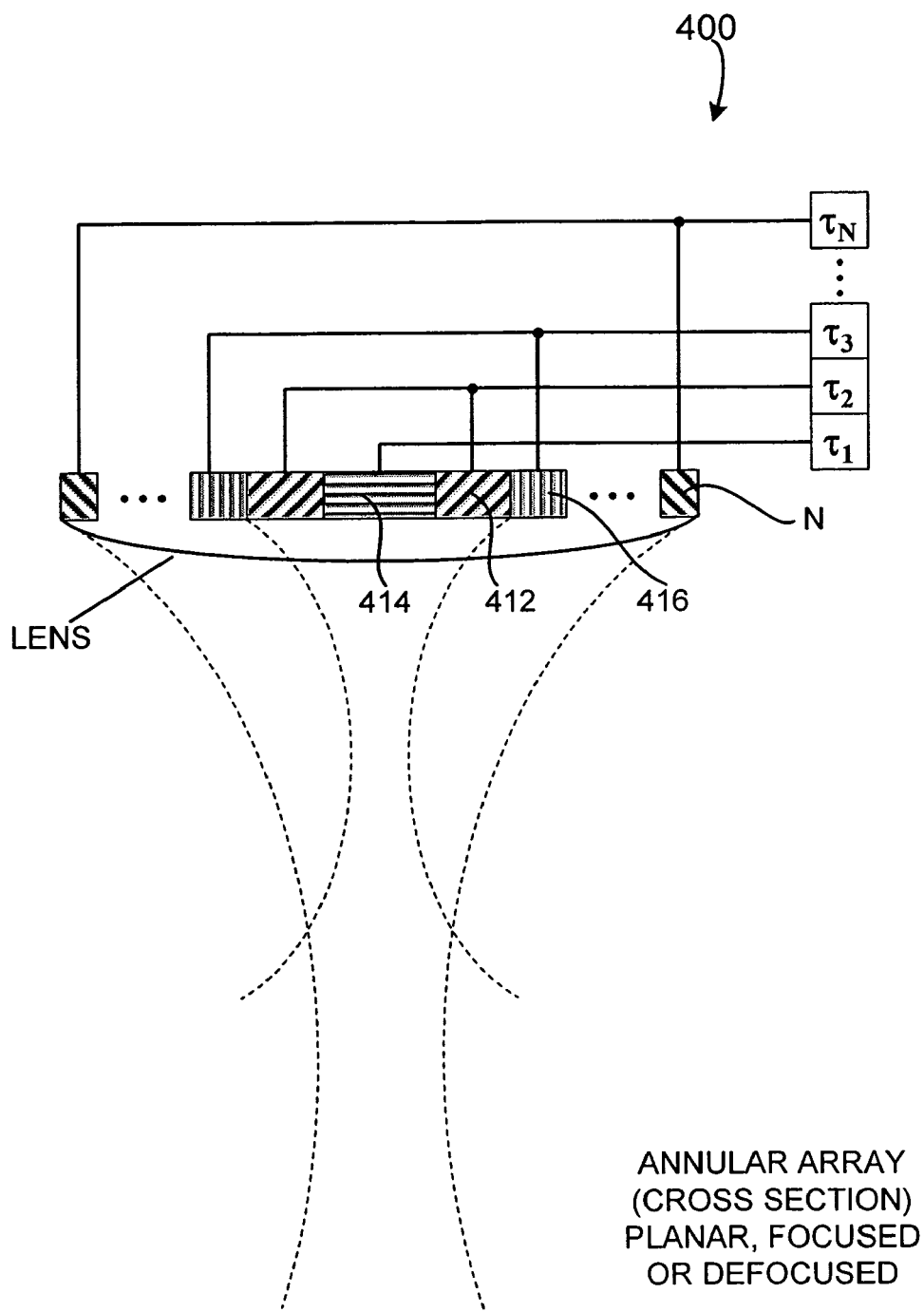
Figure 4D:
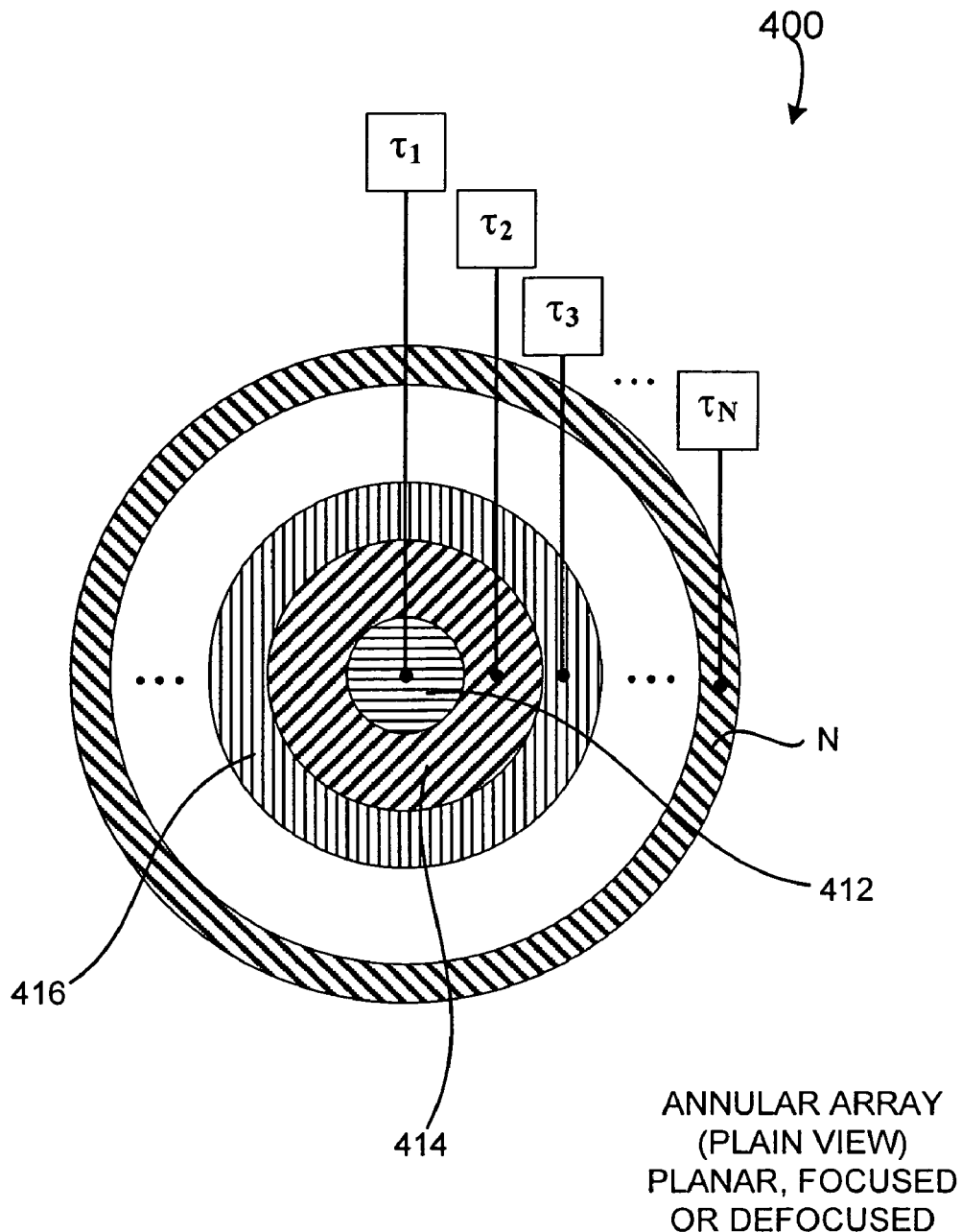

With reference to FIGS. 4C and 4D, transducer 402 can also be configured as an annular array to provide planar, focused and/or defocused acoustical energy. For example, in accordance with an exemplary embodiment, an annular array 400 can comprise a plurality of rings 412, 414, 416 to N. Rings 412, 414, 416 to N can be mechanically and electrically isolated into a set of individual elements, and can create planar, focused, or defocused waves. For example, such waves can be centered on-axis, such as by methods of adjusting corresponding transmit and/or receive delays, $\tau_1, \tau_2, \tau_3 \ldots \tau_N$. An electronic focus can be suitably moved along various depth positions, and can enable variable strength or beam tightness, while an electronic defocus can have varying amounts of defocusing. In accordance with an exemplary embodiment, a lens and/or convex or concave shaped annular array 400 can also be provided to aid focusing or defocusing such that any time differential delays can be reduced. Movement of annular array 400 in one, two or three-dimensions, or along any path, such as through use of probes and/or any conventional robotic arm mechanisms, may be implemented to scan and/or treat a volume or any corresponding space within a region of interest.

Figure 5:
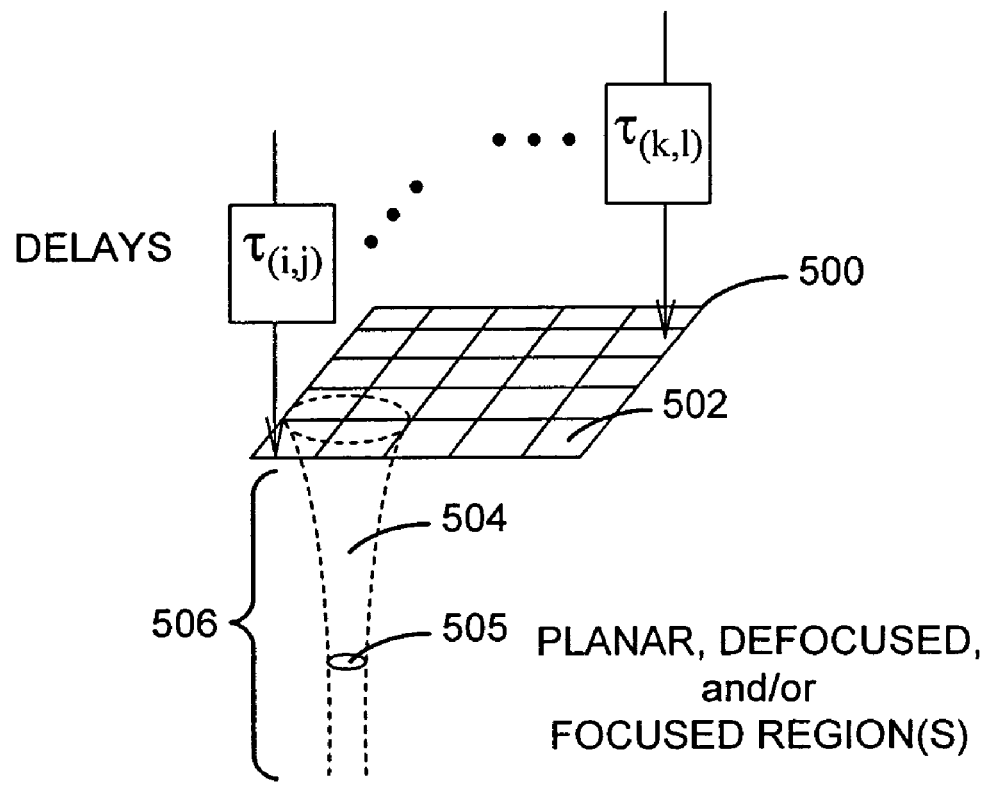
FIG. 5 is an exemplary embodiment of a transducer configured as a two-dimensional array for ultrasound treatment.

In accordance with another exemplary embodiment, transducer 202 may be suitably diced in two-dimensions to form a two-dimensional array. For example, with reference to FIG. 5, an exemplary two-dimensional array 500 can be suitably diced into a plurality of two-dimensional portions 502. Two-dimensional portions 502 can be suitably configured to focus on the treatment region at a certain depth, and thus provide respective slices 504 of the treatment region. As a result, the two-dimensional array 500 can provide a two-dimensional slicing of the image place of a treatment region, thus providing two-dimensional treatment.

In accordance with another exemplary embodiment, transducer 202 may be suitably configured to provide three-dimensional treatment. For example, to provide-three dimensional treatment of a region of interest, with reference again to FIG. 2, a three-dimensional system can comprise transducer 202 configured with an adaptive algorithm, such as, for example, one utilizing three-dimensional graphic software, contained in a control system, such as control system 208. The adaptive algorithm is suitably configured to receive two-dimensional imaging and temperature information relating to the region of interest, process the received information, and then provide corresponding three-dimensional imaging and temperature information. For example, transducer 202 may be configured with a 3D imaging and monitoring system as disclosed in U.S. patent application Ser. No. 10/193,491, entitled "Imaging, Therapy & Temperature Monitoring Ultrasonic System", filed on Jul. 10, 2002, as well as disclosed in U.S. Pat. No. 6,036,646, entitled "Imaging, Therapy & Temperature Monitoring Ultrasonic System", also having at least one common inventor and a common Assignee as the present application, and both incorporated herein by reference.

In accordance with an exemplary embodiment, with reference again to FIG. 5, an exemplary three-dimensional system can comprise a two-dimensional array 500 configured with an adaptive algorithm to suitably receive slices 504 from different image planes of the treatment region, process the received information, and then provide volumetric information 506, e.g., three-dimensional imaging and temperature information. Moreover, after processing the received information with the adaptive algorithm, the two-dimensional array 500 may suitably provide therapeutic heating to the volumetric region 506 as desired.

Alternatively, rather than utilizing an adaptive algorithm, such as three-dimensional software, to provide three-dimensional imaging and/or temperature information, an exemplary three-dimensional system can comprise transducer 202 configured within a probe arrangement to operate from various rotational and/or translational positions relative to a target region. For example, transducer 202 may be configured with a probe configuration, e.g., a manually operated or motorized probe configuration, as disclosed in U.S. Pat. No. 6,036,646, entitled "Imaging, Therapy & Temperature Monitoring Ultrasonic System", having some common inventors and a common Assignee as the present application, and incorporated herein by reference. In addition to and/or alternatively, transducer 202 may be configured with a 3D probe device disclosed in U.S. Provisional Application No. 60/570,145, entitled "3D Data Acquisition Device for Ultrasound," filed on May 12, 2004, and incorporated herein by reference.

Irrespective of the type of transducer system utilized, the size of any acoustic single and/or two-dimensional arrays, individual transducer elements, and single or multiple elements may comprise a variety of sizes to achieve the desired acoustic field distributions, such as for example from a fraction of an acoustic wavelength in size, e.g., one that radiates sound and/or ultrasound over a broad angle, up to acoustic sources that are many wavelengths in breadth, e.g., one that projects sound and/or ultrasound in a more forward directional manner.

Moreover, the physiological effects created in tissue by the exemplary combined ultrasound systems are not only affected by the spatial distribution of energy, but also the temporal, e.g., time-varying, characteristics. Thus, each array, two-dimensional array, or single element or other transducer may also be 1) used at various transmit frequencies, such as from 20 kHz to 100 MHz, or even with single broadband pulses of energy, 2) used with varied transmit pulse lengths from a millisecond to continuous wave, e.g., for seconds, minutes, or longer, 3) used with varied pulse duty cycle from almost zero percent ON time to 100% ON time, and/or 4) used with various transmit power levels from microwatts to kilowatts, depending on the total desired energy and acoustic intensity levels.

Figure 6A:
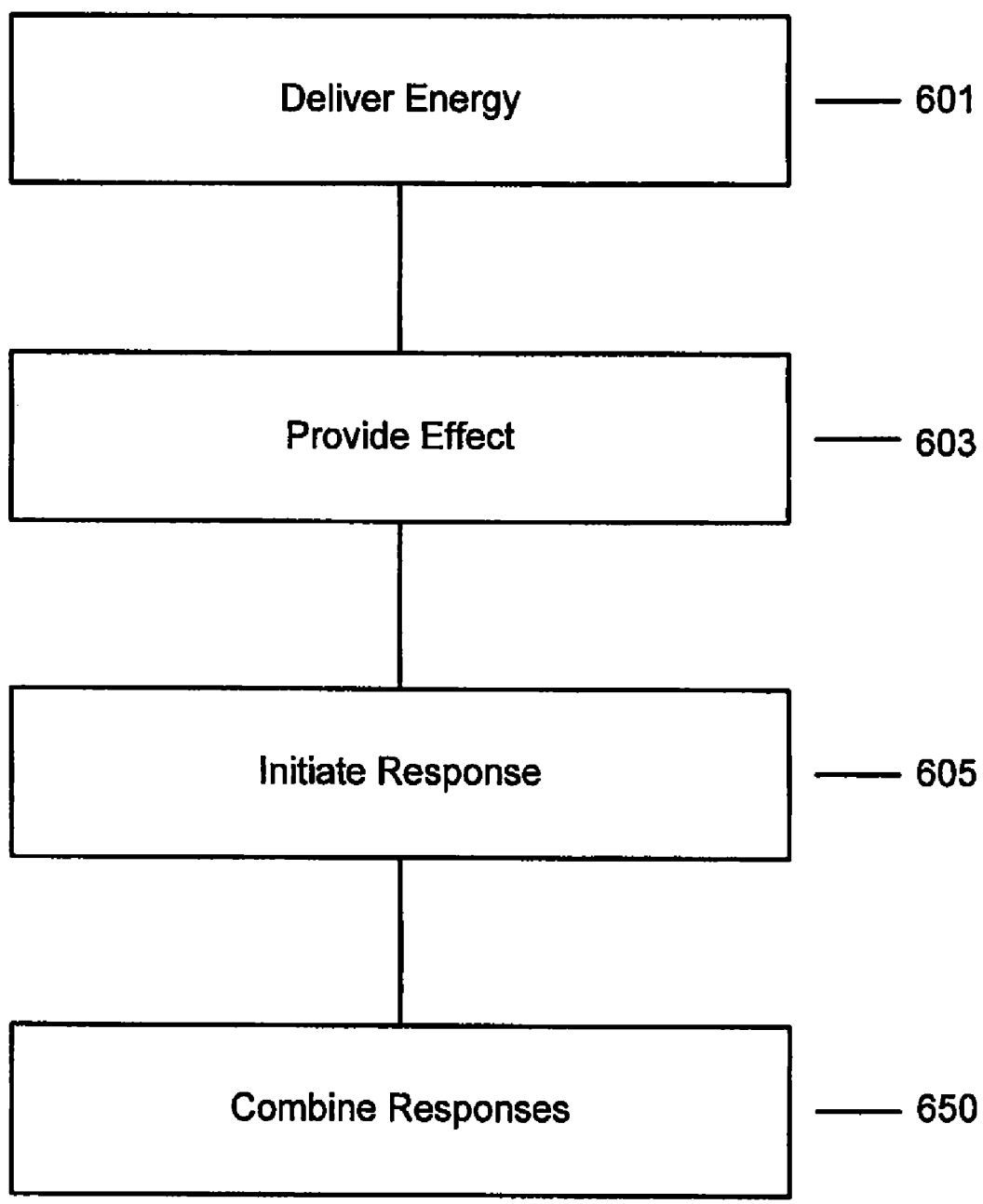
FIGS. 6A, 6B and 6C are flowcharts of methods for combined ultrasound treatment in accordance with exemplary embodiments of the present invention.
Figure 6B:
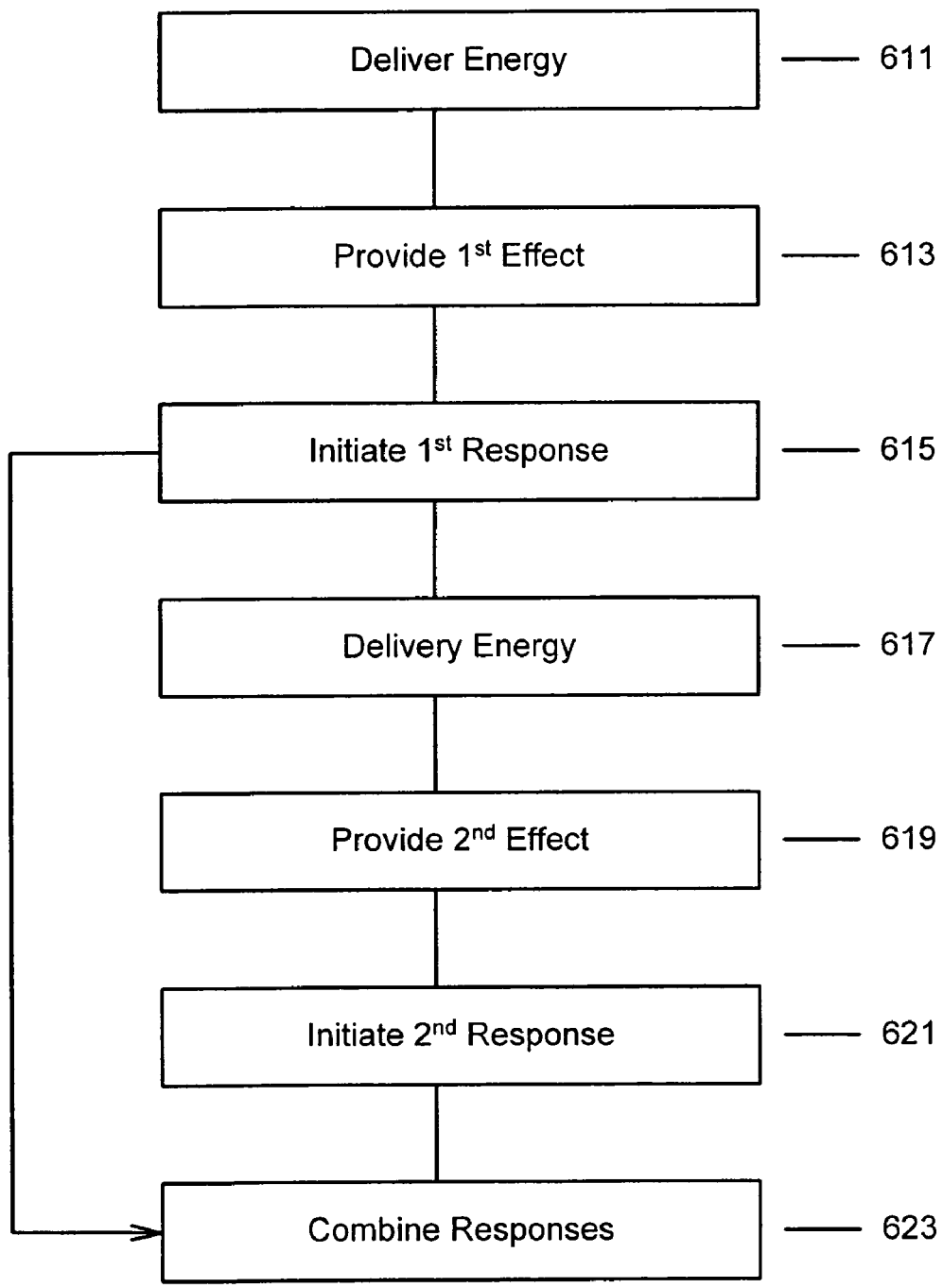

Through operation of ultrasound system 200, a method for combined ultrasound treatment can be realized that can facilitate effective and efficient therapy without creating chronic injury to human tissue. For example, with reference to FIGS. 6A, 6B and 6C, exemplary flowcharts illustrate methods for combined ultrasound treatment in accordance with various exemplary embodiments of the present invention. With particular reference to an exemplary method illustrated in FIG. 6A, a user may use a transducer to deliver energy (step 601) to a region of interest. As used herein, the term user may include a person, employee, doctor, nurse, and/or technician, utilizing any hardware and/or software of other control systems. By delivering energy, the transducer may be driven at a selected frequency, a phased array may be driven with certain temporal and/or spatial distributions, a transducer may be configured with one or more transduction elements to provide focused, defocused and/or planar energy, and/or the transducer may be configured and/or driven in any other ways hereinafter devised. Selection of the energy field for operation can be based on the type of effects and/or responses desired for an application.

The energy delivered in step 601 may provide two or more energy effects (step 603) to a region of interest. An energy effect may be any effect described herein. The energy effects, in turn, may stimulate and/or initiate one or more responses (step 605) to the region of interest. The response(s) may be any response described herein. Accordingly, two or more energy effects may provide a single response, two or more energy effects may provide two or more responses to provide treatment of a region of interest, and/or two or more energy effects may provide two or more responses that may be combined (step 650) into a single response to facilitate overall rejuvenation and treatment to the region of interest.

While an exemplary method for combined ultrasound treatment can be realized in the preceding series of steps 601, 603, 605 and 650, an exemplary method for combined ultrasound treatment may be achieved through any of the steps being performed in any order. For example, with reference to an exemplary flowchart illustrated in FIG. 6B, a user may use a transducer to deliver energy (step 611) to a region of interest. The energy may be delivered through a phase array with certain temporal and/or spatial distributions, through a transducer configured with one or more transduction elements to provide focused, defocused and/or planar energy, and/or through a transducer configured and/or driven any other way described herein and/or hereinafter devised. The energy may be used to provide a first energy effect (step 613) to a region of interest. The first effect may be any effect described herein. The first effect, in turn, may initiate and/or stimulate a first response (step 615) to a region of interest. The first response may be any response described herein.

The transducer may also be configured to deliver energy again (step 617) to provide a second energy effect (step 619) to the same and/or different region of interest, initiating and/or stimulating a second response or combining with the first energy effect to provide the first response (step 621) to the same and/or different region of interest. By delivering energy for a second time, the transducer may be driven at the same frequency as in step 611 and/or at a different frequency than that of step 611. The second effect and second response may be any effect and response described herein. The first and second effects and/or responses may occur instantaneously and/or may develop over a longer duration period, such as, for example, one week, with one or more delay periods in between. In the event that the first and second effect produce two or more responses, the two or more of the responses may also be combined (step 650) to facilitate overall rejuvenation and treatment to the region of interest.

Figure 6C:
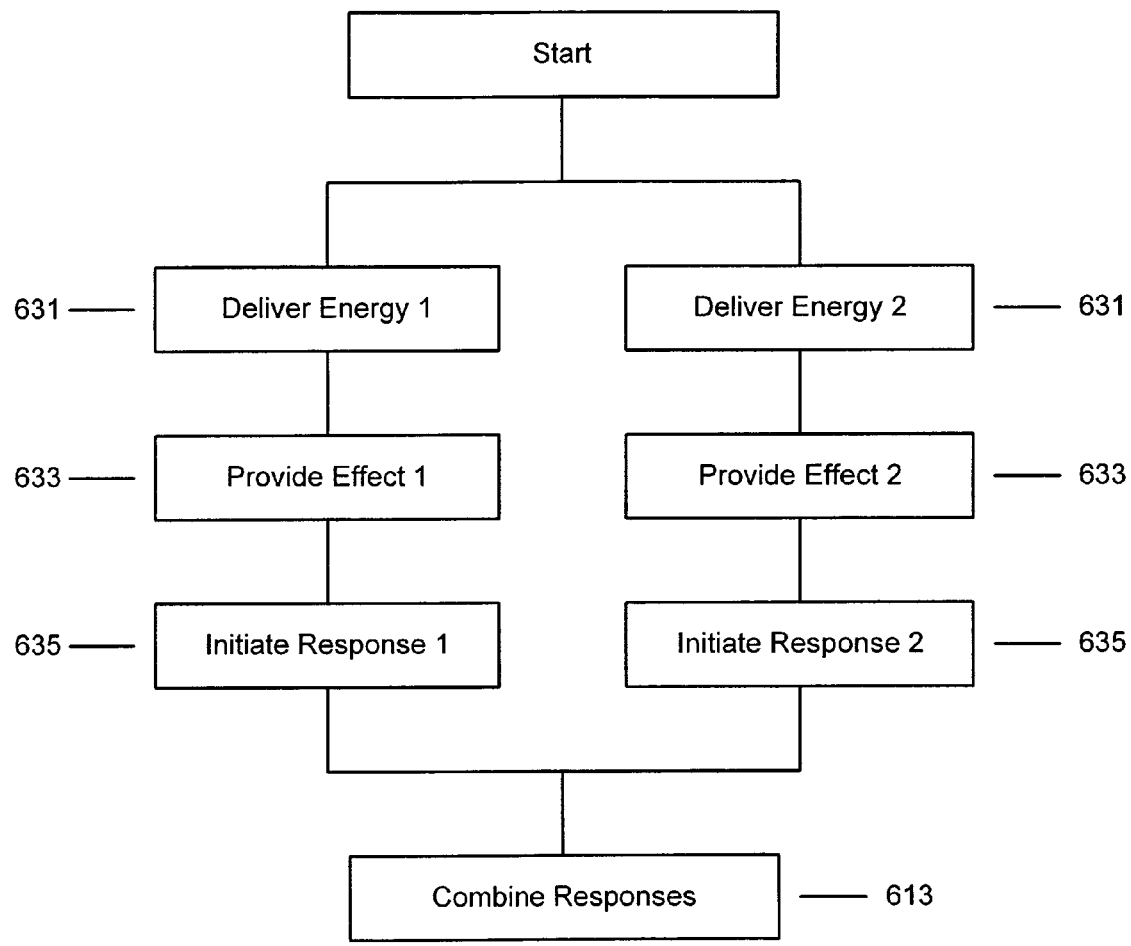

Another example of an exemplary method for combined ultrasound treatment is illustrated in FIG. 6C. A user may use a transducer to deliver one or more energy fields (step 631) to a region of interest. By delivering energy, the transducer may be driven at a certain frequency, a phase array may be driven with certain temporal and/or spatial distributions, a transducer may be configured with one or more transduction elements to provide focused, defocused and/or planar energy, and/or the transducer may be configured and/or driven any other ways hereinafter devised. The energy fields may be delivered simultaneously, the energy may be delivered at delayed and/or overlapping times, and/or the energy may be delayed at different times altogether.

Each energy field delivered may provide one or more energy effects (step 633) to a region of interest. The energy effects may be any effects described herein. Each energy effect may initiate and/or stimulate and provide and/or combine one or more responses (step 635) to the same and/or a different region of interest. The responses may be any response described herein. The energy effects and/or responses may occur instantaneously, simultaneously, and/or may develop over a longer duration period, such as, for example, one week. Two or more of the responses may be combined (step 650) to facilitate overall rejuvenation and treatment to the region of interest. While the present invention describes a method for combined ultrasound treatment in the preceding series of steps, the method of the present invention may be achieved through any of the steps being performed in any order.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. Further, it should be noted that while the method and system for combined ultrasound treatment with a transducer is described above is suitable for use by a medical practitioner proximate the patient, the system can also be accessed remotely, i.e., the medical practitioner can view through a remote display having imaging information transmitted in various manners of communication, such as by satellite/wireless or by wired connections such as IP or digital cable networks and the like, and can direct a local practitioner as to the suitably placement for the transducer. These and other changes or modifications are intended to be included within the scope of the present invention, as set forth in the following claims.

The invention claimed is:

1. An ultrasound system configured for providing treatment comprising:
a single ultrasound transducer comprising a first portion providing a first ultrasound energy effect and a second portion providing a second ultrasound energy effect to a region of interest, wherein said first portion and said first ultrasound energy effect are different from said second portion and said second ultrasound energy effect, and said first ultrasound energy effect comprises an ablative or a hemostatic effect and said second ultrasound energy effect comprise at least ~ one of non-thermal streaming, hydrodynamic, diathermic, and resonance induced tissue effects;
a control system that is connected to said first portion and to said second portion and configured to operatively control said first portion independently of said second portion; and wherein said first energy effect and said second energy effect are configured to effect said region of interest to facilitate at least one response in said region of interest and said control system controls said second portion to provide said second energy effect after a delay period after said first energy effect.

2. The ultrasound treatment system according to claim 1, wherein said first portion and said second portion simultaneously provide said first energy effect and said second energy effect to achieve a simultaneous response in said region of interest.

3. The ultrasound treatment system according to claim 1, wherein said region of interest comprises at least one of a superficial, subcutaneous, and an inner region of a patient.

4. The ultrasound treatment system according to claim 1, wherein said single ultrasound transducer comprises a variable-thickness transduction element.

5. The ultrasound treatment system according to claim 1, wherein said first portion comprises a transduction element configured for low frequency treatment and said second portion comprises a transduction element configured for high-frequency treatment.

6. The ultrasound treatment system according to claim 1, wherein said single ultrasound transducer comprises an array configured for providing a focused treatment.

7. The ultrasound treatment system according to claim 1, wherein said ultrasound transducer comprises am electronic focusing array.

8. The ultrasound treatment system according to claim 1, wherein said single ultrasound transducer comprises an annular array.

9. An ultrasound treatment system according to claim 1, wherein said at least two ultrasound energy effects are configured to facilitate at least two responses in said region of interest.

10. An ultrasound system according to claim 1, wherein said ultrasound treatment system further comprises a coupling system configured for acoustic coupling between said single ultrasound transducer and the region of interest.

11. An ultrasound system according to claim 10, wherein said coupling system is configured for controlled cooling of an interface surface proximate to a region of interest to facilitate control of thermal energy effects of said ultrasound treatment system.

12. An ultrasound system according to claim 1, wherein said ultrasound treatment system is configured for providing at least one of therapy, imaging and tissue parameter monitoring.

13. An ultrasound system according to claim 10, wherein said ultrasound treatment system is configured for providing combined therapy and imaging treatment.

14. A method for providing non-invasive ultrasound treatment to a patient, said method comprising:
operating a transducer emitting ultrasound energy at a first frequency range to provide a first energy effect comprising an ablative or a hemostatic effect to produce a first response in a region of interest; and
operating said transducer emitting ultrasound energy at a second frequency range to provide a second energy effect comprising a non-thermal streaming effect that is distinct from and independent of said first energy effect and occurs after one or more delay periods after said first energy effect.

15. The method according to claim 14, wherein said ultrasound energy emitted at said second frequency range and amplitude is emitted by a control system applying more power to said transducer than occurs when said ultrasound energy at said first frequency range and amplitude is emitted.

16. The method according to claim 15, wherein said method further comprises combining said first response and said second response to produce an overall response in said region of interest.

17. The method according to claim 14, wherein said further comprises a cavitational, hydrodynamic, and a resonance induced tissue effect.

18. The method according to claim 14, wherein said second energy effect further comprises a cavitational, and hydrodynamic, tissue effect.

19. The method according to claim 14, wherein said step of operating a transducer emitting ultrasound energy at a first frequency range and amplitude to provide said first energy effect to produce a first response in a region of interest comprises operating a transducer emitting ultrasound energy to produce at least one of a hemostasis, subsequent revascularization/angiogenesis, coagulative necrosis, growth of interconnective tissue, tissue reformation, ablation of existing tissue, collagen reformation, enhanced delivery and activation of medicants, stimulation of protein synthesis and increased cell permeability response.

20. The method according to claim 14, wherein said step of operating a transducer emitting ultrasound energy at a second frequency range and amplitude to provide a second energy effect to produce a second response in a region of interest comprises operating a transducer emitting ultrasound energy to produce at least one of a second hemostasis, subsequent revascularization/angiogenesis, growth of interconnective tissue, tissue reformation, ablation of existing tissue, collagen reformation, enhanced delivery and activation of medicants, stimulation of protein synthesis and increased cell permeability response, and wherein said second response is the same as or different from said first response.

21. A method for providing non-invasive ultrasound treatment to a patient, said method comprising:
providing one of a first planar, defocused, or focused ultrasound energy beam to a region of interest to produce a first energy effect comprising an ablative or hemostatic effect and a corresponding first response;
allowing a delay period to occur after producing said first energy effect; and
providing one of a second planar, defocused, or focused ultrasound energy beam to said region of interest to produce a second energy effect comprising a non-thermal streaming effect and a corresponding second response wherein said first planar, defocused, or focused ultrasound energy beam and said second planar, defocused, or focused ultrasound energy beam are capable of creating said first response and said second response.

22. The method according to claim 21, wherein said first energy effect further comprises providing one of a first planar, defocused, and focused ultrasound energy beam to a region of interest to produce one of a thermal, cavitational, hydrodynamic, and a resonance induced tissue effect.

23. The method according to claim 21, wherein said second energy effect further comprises providing one of a second planar, defocused, and focused ultrasound energy beam to a region of interest to produce one of a thermal, cavitational, hydrodynamic, and a resonance induced tissue effect, and wherein said second energy effect is the same as or different from said first energy effect.

24. The method according to claim 21, wherein said step of providing one of a first planar, defocused, and focused ultrasound energy beam to a region of interest to produce a first response comprises providing one of a first planar, defocused, and focused ultrasound energy beam to a region of interest to produce one of a hemostasis, subsequent revascularization/angiogenesis, growth of interconnective tissue, tissue reformation, ablation of existing tissue, collagen reformation, enhanced delivery and activation of medicants, stimulation of protein synthesis and increased cell permeability response.

25. The method according to claim 21, wherein said step of providing one of a second planar, defocused, and focused ultrasound energy beam to a region of interest to produce a second response comprises providing one of a first planar, defocused, and focused ultrasound energy beam to a region of interest to produce one of a hemostasis, subsequent revascularization/angiogenesis, growth of interconnective tissue, tissue reformation, ablation of existing tissue, collagen reformation, enhanced delivery and activation of medicants, stimulation of protein synthesis and increased cell permeability response, and wherein said second response is the same as or different from said first response.

26. The ultrasound system according to claim 1, wherein said single ultrasound transducer further comprises a backing layer and a matching layer attached to said first portion.

27. The ultrasound system according to claim 1, wherein said single ultrasound transducer further comprises a first backing layer and a first matching layer attached to said first portion and a second backing layer and second matching layer attached to said second portion wherein said first backing layer and matching layer are structurally different from said second backing layer and second matching layer.

28. The method according to claim 14, wherein said ultrasound energy is emitted at said first frequency range and amplitude and also emitted at a harmonic frequency range.

* * * * *

UNITED STATES PATENT AND TRADEMARK OFFICE
CERTIFICATE OF CORRECTION

PATENT NO. : 7,530,958 B2  Page 1 of 1
APPLICATION NO. : 10/950112
DATED : May 12, 2009
INVENTOR(S) : Slayton et al.

It is certified that error appears in the above-identified patent and that said Letters Patent is hereby corrected as shown below:

Column 7, line 42 include a period after "reference".

Column 7, line 47 capitalize the "D" in "Multi-directional" making it "Multi-Directional".

Column 11, line 60 in Claim 1 delete "~".

Column 12, line 25 in Claim 7 replace "am" with "an".

Signed and Sealed this

Twenty-first Day of July, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,530,958 B2  Page 1 of 1
APPLICATION NO. : 10/950112
DATED : May 12, 2009
INVENTOR(S) : Slayton et al.

It is certified that error appears in the above-identified patent and that said Letters Patent is hereby corrected as shown below:

Title Page; item (73);

On cover sheet under Assignee replace "Inc." with "L.L.C."

Signed and Sealed this

First Day of December, 2009

David J. Kappos
*Director of the United States Patent and Trademark Office*